(12) United States Patent  
Vick

(10) Patent No.: US 6,749,479 B2
(45) Date of Patent: Jun. 15, 2004

(54) SCENT EMITTING SOFT TOY

(76) Inventor: T. Kevin Vick, 113 Pony Cir., Thomasville, GA (US) 31792

( * ) Notice: Subject to any disclaimer, the term of this patent is extended or adjusted under 35 U.S.C. 154(b) by 0 days.

(21) Appl. No.: 09/971,356

(22) Filed: Oct. 4, 2001

(65) Prior Publication Data

US 2003/0068955 A1 Apr. 10, 2003

(51) Int. Cl.$^7$ ................................................ A63H 3/00
(52) U.S. Cl. ........................... 446/73; 446/72; 446/369
(58) Field of Search ........................... 446/369, 71, 73, 446/75, 76, 77, 385, 72; 215/382

(56) References Cited

U.S. PATENT DOCUMENTS

| 2,720,419 | A | | 10/1955 | Eby | |
|---|---|---|---|---|---|
| 2,766,067 | A | | 10/1956 | Shinberg | |
| 4,143,784 | A | * | 3/1979 | Frahm et al. | 215/12.1 |
| 4,476,171 | A | | 10/1984 | Takeuchi | |
| 4,607,674 | A | * | 8/1986 | Noble | 206/389 |
| 4,889,284 | A | * | 12/1989 | Spector | 239/34 |
| 5,037,343 | A | * | 8/1991 | Benites | 446/268 |
| 5,172,863 | A | * | 12/1992 | Melone et al. | 239/211 |
| 5,456,626 | A | * | 10/1995 | Ming-Kang | 446/397 |
| 5,676,583 | A | * | 10/1997 | Wang et al. | 446/268 |
| 5,897,421 | A | | 4/1999 | Rink et al. | |
| 6,012,963 | A | | 1/2000 | Lee | |
| 6,089,947 | A | * | 7/2000 | Green | 446/268 |
| 6,193,577 | B1 | * | 2/2001 | Kaplan | 446/72 |
| 6,422,912 | B1 | * | 7/2002 | Summers | 446/184 |
| 6,520,826 | B2 | * | 2/2003 | Spector | 446/73 |

OTHER PUBLICATIONS

U.S. 2001/0027958 A1: Short et al, Container, cover, and insert for a consumer product, Oct. 11, 2001.*

* cited by examiner

Primary Examiner—Jacob K. Ackun
Assistant Examiner—Faye Francis
(74) Attorney, Agent, or Firm—Baker, Donelson, Bearman, Caldwell & Berkowitz

(57) ABSTRACT

A stuffed, soft body scent-emitting figurine (10) defined by a fabric material (12) and having an internal cavity filled with a stuffing material receives a chamber (16) having a bottom and side walls. A scent material (25) is received in the chamber. A cap (26) defines openings (32) for communicating scent from the chamber (16).

18 Claims, 2 Drawing Sheets

SCENT EMITTING SOFT TOY

TECHNICAL FIELD

The present application relates to toys. More particularly, the present invention is directed to soft, stuffed toys for play while emitting desirable scenting of the air.

BACKGROUND OF THE INVENTION

Stuffed, soft bodied animal and personage characters have long been a favorite toy for young children. Rarely are a group of young children seen, such as at airports, camps, and the like, where at least some of the children are carrying stuffed animals or characters. These play toys are readily huggable and have a comforting effect on the children. These toys typically are manufactured from fabric materials that is cut and attached together to define bodies with various appropriate appendages. The bodies are then filled with various stuffing materials, typically soft, but firm materials are used as well. The characters often are popularly known cartoon or other characters, as well as replicas of animals and the like.

These stuffed animal and personage characters are held, played with, and otherwise used in many different locations, but generally at the home of the owner of the toy. It is to be appreciated that these various environments have differing smells and odors. Often persons attempt to modify or control the odors, and there are a variety of devices directed to such. Further, it is believed that persons may be helped in attitude and comfort if the odors in their environment are pleasing and satisfactory rather than unpleasant or disturbing.

The scenting devices heretofore known have, while providing for the scenting of air typically in bathrooms or in heating and ventilation systems, have not been entirely successful in being incorporated with articles used by children to provide a favorable fragrance in their various environments.

Accordingly, there is a need in the art for improved soft stuffed toys for entertaining children while providing desirable scenting for playrooms. It to such that the present invention is directed.

BRIEF DESCRIPTION OF THE PRESENT INVENTION

The present invention meets the need in the art for an improved toy for entertaining children while providing desirable scenting for playrooms by providing a stuffed, soft body scent-emitting toy in which a figurine is defined by an exterior surface of a fabric material and having an internal cavity filled with a stuffing material to define a body thereof. A portion of the fabric material defines an opening which receives a chamber having a bottom and side wall extending in a first direction. A cap is sized for removably engaging the distal edge portion of the side wall of the chamber. The cap defines a plurality of spaced-apart openings for communicating air through the cap. The figurine, receiving a scent emittive material in the chamber closed by the cap, provides a soft toy that emits a scent through the openings.

Objects, features, and advantages of the present invention will become apparent from a reading of the following detailed description of the invention and claims in view of the appended drawings.

DETAILED DESCRIPTION OF THE PREFERRED EMBODIMENTS

Figure 1:
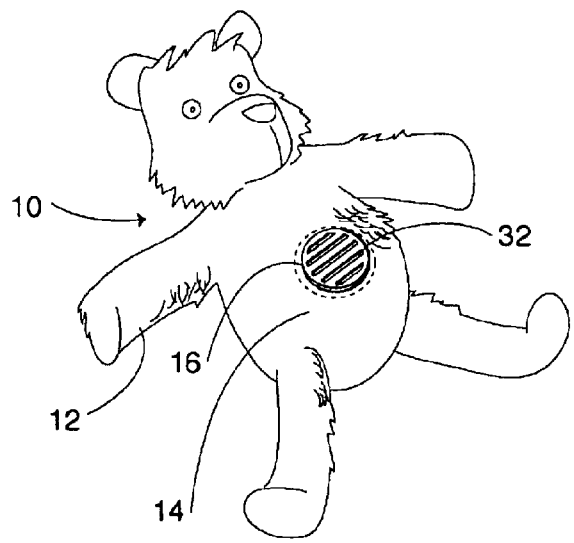
FIG. 1 illustrates in perspective view an embodiment of a stuffed, soft body scent-emitting toy according to the present invention.

Referring now in more detail to the drawings, in which like numerals indicate like parts throughout the several views, FIG. 1 is a perspective view of an embodiment of a stuffed, soft body scent-emitting toy 10 according to the present invention. The toy 10 comprises a character-ornamented figurine, and by this is meant that the toy has character attributes such as arms, legs, head, and the like associated with a character. In the illustrated embodiment, the character is a bear-like creature, but the toy can be any number of configurations based on artistic inclination. A fabric material generally 12 defines an exterior surface which is cut and attached together, such as by sewing, sonic welding, or the like to define a body of the toy 10. The body defines an internal cavity which is filled with a conventional stuffing material 11 (see FIG. 2) to define volumetric dimensions of the body of the toy 10. A portion 14 of the fabric material 12 defines an opening which receives a chamber 16.

Figure 2:
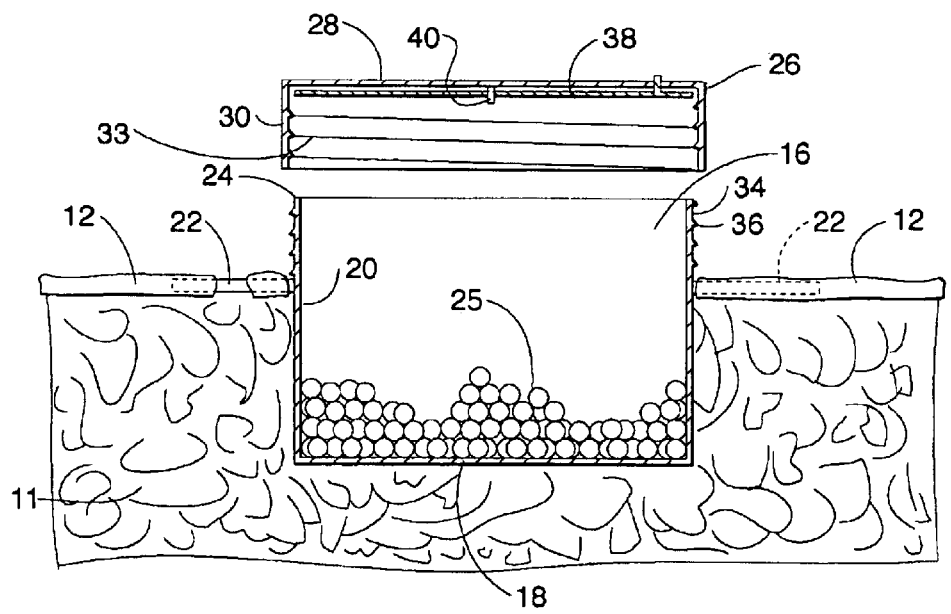
FIG. 2 is a side cross-sectional view taken along line 2—2 in FIG. 1, to illustrate features of the invention.

The chamber 16 is better illustrated in cross-sectional view in FIG. 2. The chamber 16 includes a bottom 18 and side wall 20 extending in a first direction. A flange 22 illustrated in partial cut-away view extends laterally about a perimeter of the chamber. The flange 22 is disposed spaced apart and remote from the bottom 18 but recessed relative to a distal edge 24 of the side wall 20. The chamber 16 receives and holds articles, such as scent materials 25. The scent materials 25 can be a plurality of conventional scent beads, provided to the chamber 16 either a group of loose beads or contained within a package, or other scent material conventional in the trade.

A cap 26 includes a plate 28 and a skirt 30 that extend a predetermined distance from a perimeter edge of the plate 28. The cap 26 is sized for removably engaging the distal edge portion of the side wall 20 of the chamber 16. As best illustrated in FIG. 1, the plate 28 defines a plurality of spaced-apart openings 32 for communicating air from the chamber 16. The openings 32 are illustrated as substantially rectangular cut-outs, but other patterns can be employed, such circular (see the embodiment in FIG. 3, curvilinear (see the embodiment in FIG. 4), or other pattern. In the illustrated embodiment, the interior surface of the skirt 30 defines a thread 33.

The flange 22 and the fabric material 12 around the opening in the portion 14 connect together, whereby the chamber 16 is held in the body of the toy 10. The fabric material 12 connects to the flange 22 preferably by an adhesive, although the flange 22 can be sown to the fabric material with a cord or thread, connected with rivets, secured with sonic welding, or other similar engagement mechanism.

A distal edge portion 34 of the side wall 20 extends slightly outwardly of the body of the toy 10. The distal end portion 34 defines a thread 36 on the exterior surface. The thread 36 engages the thread 33 of the cap to secure the cap to the chamber 16.

Figure 4:
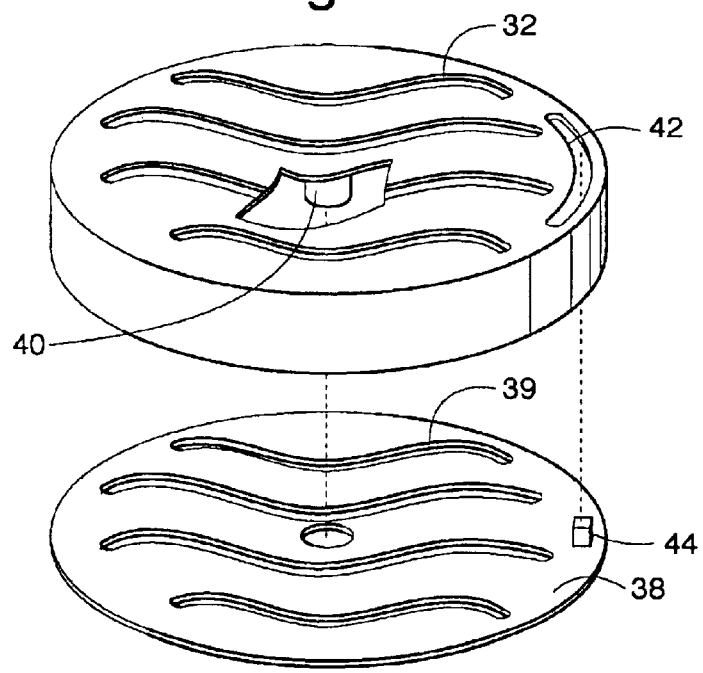
FIG. 4 is an exploded view of the cap for closing the chamber in the toy illustrated in FIG. 1.

The cap 26 includes a rotatable disk 38 that defines openings 39 (see FIG. 4) corresponding substantially to the openings 32 in the plate 28. FIG. 4 illustrates an alternate embodiment in exploded view with a different configuration of openings 32, 39 to suggest the possible variations. The disk 38 connects by a pin 40 extending from a central portion of the plate 28. The openings 39 in the disk 38 selectively register with the openings 32, so that the effective cross-sectional area of the openings through the cap can be changed to adjust the volume of air communicated through the openings.

With continued reference to FIGS. 2 and 4, the plate 38 further defines an arcuate slot 42 in a side portion. The disk 38 includes a tab 44 that projects through the arcuate slot 42. The tab 44 permits the disk 38 to be rotated between between a first position at a first end of the arcuate slot 42 and a second position at an opposing end of the arcuate slot. Stopping the tab 44 at an intermediate position brings the openings in the disk 38 into at least partial registration with the openings in the plate 28, for varying selectively the communication of air from the chamber 16.

Figure 3:
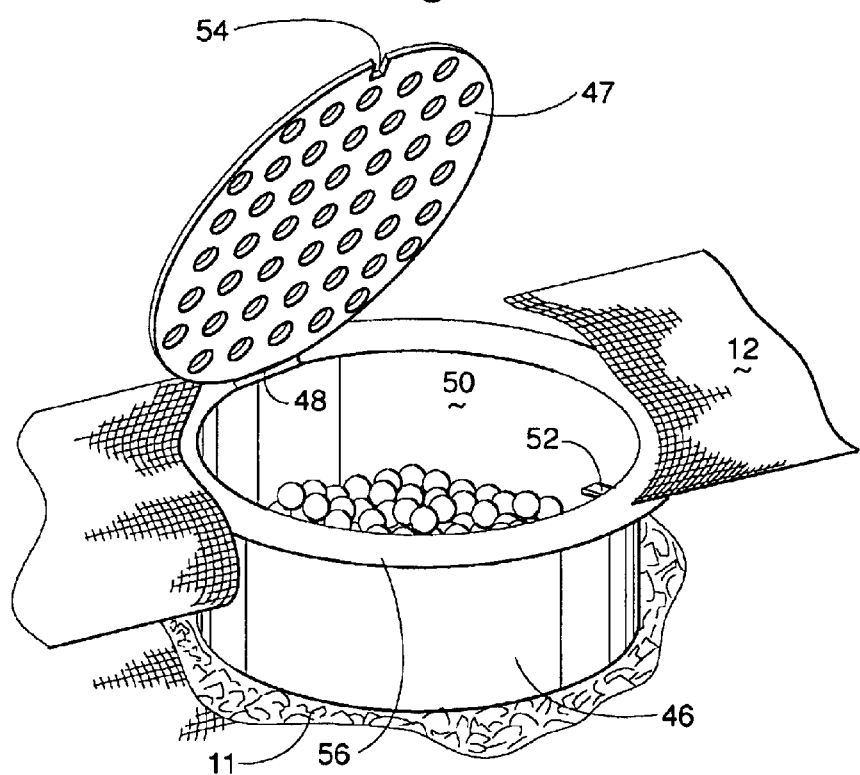
FIG. 3 is a perspective view of an alternate embodiment of a chamber received in the soft body toy illustrated in FIG. 1.

FIG. 3 is a perspective view of an alternate embodiment of a chamber 46 received in the soft body toy 10 illustrated in FIG. 1. In this embodiment, a cap 47 connects by a hinge 48 at an edge of a side wall 50 of the chamber 46. A pin 52 extends radially from an inner wall surface near the distal edge of the side wall 50. The cap 47 defines a slot 54 in the skirt in alignment with the pin 52. The cap 47 pivots closed on the hinge 48 and is secured closed by engaging the pin 52 in the slot 54 of the cap. It is to be appreciated that other fastening mechanisms can be gainfully used to hold the cap to the chamber, such as a groove and projecting ring that interlock, a flap extending laterally from the sidewall 50 which flap overlaps a side edge of the cap 47 and locks to a tab protruding from an exterior surface of the cap, and other such latching structures. In the embodiment illustrated in FIG. 3, a flange 56 extends laterally at a distal edge of the side wall 50, for engaging the chamber 46 to the fabric material 12, as discussed above.

The toy 10 is used as plaything, such as by children. The chamber 16 receives the scent material 25, and the cap 26 is closed. In the illustrated embodiment, the cap 26 threadingly engages the thread 36 on the side wall 20. The scent material 25 volatilizes, and scent vapors communicate through the openings 32 in the cap 26. The strength of the scent emitted by the toy 10 can be adjusted. This is accomplished by moving the tab 44 in the slot 42. To reduce the scent, the openings in the disk 38 are taken out of registration with the openings in the plate 38. This reduces the cross-sectional area of the openings, which allows a smaller volume of scent to be communicated. Conversely, to increase the effect of the scent, the openings are brought into registration to increase the cross-sectional area for communication of the scent. It is to be appreciated that other control mechanisms such as louvers, sliding covers, and the like, can be used. Upon expiration of the effectiveness of the scent material 25, the cap 26 is opened and the scent material replaced. A variety of fragrances are commercially available from fragrance suppliers to meet the various personal preferences of persons using the toy 10.

The present invention accordingly provides the stuffed, soft body scent-emitting toy suitable for comfort and play while selectively scenting the air. The principles, preferred embodiments, and modes of operation of the present invention have been described in the foregoing specification. The invention is not to be construed as limited to the particular forms disclosed because these are regarded as illustrative rather than restrictive. Moreover, variations and changes may be made by those skilled in the art without departure from the spirit of the invention as described by the following claims.

What is claimed is:

1. A stuffed, soft body scent-emitting toy, comprising:
    a figurine defined by an exterior surface of a fabric material and having an internal cavity filled with a stuffing material to define a body thereof, a portion of the fabric material defining an opening therein;
    a chamber having a bottom and side wall extending in a first direction therefrom and received in the opening of the figurine;
    a cap sized for removably engaging a distal edge portion of the side wall of the chamber, the cap defining a plurality of spaced-apart openings for communicating air therethrough; and
    means for changing the cross-sectional area of the openings in the cap, for changing the volume of scented air communicated through the openings,
    whereby the figurine, receiving a scent emittive material in the chamber closed by the cap, provides a soft toy that emits a scent through the openings.

2. The stuffed, soft body scent-emitting toy as recited in claim 1,
    wherein the distal end portion of the side wall is threaded on an exterior surface thereof; and
    wherein the cap is threaded on an interior surface,
    whereby the cap is threadingly engaged to the chamber.

3. The stuffed, soft body scent-emitting toy as recited in claim 1, wherein the cap is hingedly connected at an edge portion to the side wall of the chamber; and further comprising:
    a pin extending radially from an inner wall surface near the distal edge of the side wall; and
    the cap defines a slot in alignment with the pin,
    whereby the cap, being pivoted closed on the hinge connection, is secured closed by engaging the pin in the slot of the cap.

4. The stuffed, soft body scent-emitting toy as recited in claim 1, wherein means for changing comprises a disk having a plurality of openings which are registerable with the openings in the cap, the disk rotatably mounted to the cap by a pin extending from a central portion of the cap through the disk.

5. The stuffed, soft body scent-emitting toy as recited in claim 4, wherein the cap further defines an arcuate slot in a side portion thereof; and
    wherein the disk has a tab projecting therefrom through the arcuate slot in the cap,
    whereby the tab is moved selectively between a first position at a first end of the arcuate slot and a second position at an opposing end of the arcuate slot, and being selectively stopped therebetween, brings the openings in the disk into at least partial registration with the openings in the cap, for varying selectively the communication of scent from the chamber.

6. The stuffed, soft body scent-emitting toy as recited in claim 1, wherein the chamber further comprises a flange extending laterally about a perimeter thereof.

7. The stuffed, soft body scent-emitting toy as recited in claim 6, wherein the flange is disposed remote from the bottom and spaced from a distal edge of the side wall.

8. The stuffed, soft body scent-emitting toy as recited in claim 6, further comprising means for engaging the flange of the chamber to the fabric material about the perimeter of the opening in the figurine, whereby the chamber is fixingly secured to the body of the figurine.

9. A stuffed, soft body scent-emitting character, comprising:
    a fabric material defining an exterior form for a body of a character and a body cavity, the body cavity filled with a stuffing material to provide volumetric definition of the character, with an opening defined in a portion of the fabric material;

a closable chamber having a bottom and side wall extending in a first direction therefrom and received in the opening of the fabric material, with a flange extending laterally about a perimeter thereof, the flange disposed remote from the bottom and spaced from a distal edge of the side wall;

means for securing the flange to the fabric material near the opening in the fabric material;

a cap defining a plurality of openings therein for communicating air therethrough and sized for removably engaging a distal edge portion of the side wall of the chamber; and means for changing a cross-sectional area of the openings in the cap, for changing the volume of scented air communicated through the openings, whereby the character, receiving a scent emittive material in the chamber closed by the cap, provides a soft toy that emits a scent through the openings.

10. The stuffed, soft body scent-emitting character as recited in claim 9, wherein the distal end portion of the side wall is threaded on an exterior surface thereof; and wherein the cap is threaded on an interior surface, whereby the cap is threadingly engaged to the chamber.

11. The stuffed, soft body scent-emitting toy as recited in claim 9, wherein the cap is hingedly connected at an edge portion to the side wall of the chamber; and further comprising:

a pin extending radially from an inner wall surface near the distal edge of the side wall; and the cap defines a slot in alignment with the pin, whereby the cap, being pivoted closed on the hinge connection, is secured closed by engaging the pin in the slot of the cap.

12. The stuffed, soft body scent-emitting toy as recited in claim 11, wherein means for changing comprises an interior disk having a plurality of openings which are registerable with the openings in the plate, the disk rotatably mounted to the plate by a pin extending from a central portion of the plate through the disk.

13. The stuffed, soft body scent-emitting toy as recited in claim 12, wherein the plate further defines an arcuate slot in a side portion thereof and wherein the disk has a tab projecting therefrom through the arcuate slot in the plate, whereby the tab is moved selectively between a first position at a first end of the arcuate slot and a second position at an opposing end of the arcuate slot, and being selectively stopped therebetween, brings the openings in the disk into at least partial registration with the openings in the plate, for varying selectively the communication of scent from the chamber.

14. A stuffed, soft body scent-emitting character, comprising:

a fabric material defining an exterior form for a body of a character and a body cavity defined thereby filled with a stuffing material to provide volumetric definition of the character, with an opening defined in a portion of the fabric material;

a closable chamber having a bottom and side wall extending in a first direction therefrom and received in the opening of the fabric material, with a flange extending laterally about a perimeter thereof, the flange disposed remote from the bottom and spaced from a distal edge of the side wall;

means for securing the flange to the fabric material near the opening in the fabric material;

a cap defined by a plate and a skirt extending about a perimeter thereof and defining a plurality of openings in the plate for communicating air therethrough, with an arcuate slot defined in a side portion of the plate and a pin extending from a central portion thereof, the cap sized for removably engaging a distal edge portion of the side wall of the chamber;

a disk having a plurality of openings which are conformable with the openings in the plate, the disk rotatably mounted to the plate by the pin extending therethrough, and a tab projecting from a side portion of the plate for alignment with the arcuate slot in the plate, whereby the tab is moved selectively between a first position at a first end of the arcuate slot and a second position at an opposing end of the arcuate slot and being selectively stopped therebetween, brings the openings in the disk into at least partial registration with the openings in the plate, for varying selectively the communication of scent from the chamber, whereby the character, receiving a scent emittive material in the chamber closed by the cap, provides a soft toy that emits a scent through the openings.

15. The stuffed, soft body scent-emitting character as recited in claim 14, wherein the distal end portion of the side wall is threaded on an exterior surface thereof; and wherein the cap is threaded on an interior surface, whereby the cap is threadingly engaged to the chamber.

16. The stuffed, soft body scent-emitting toy as recited in claim 14, wherein the cap is hingedly connected at an edge portion to the side wall of the chamber; and further comprising:

a pin extending radially from an inner wall surface near the distal edge of the side wall; and the cap defines a slot in the skirt thereof in alignment with the pin, whereby the cap, being pivoted closed on the hinge connection, is secured closed by engaging the pin in the slot of the cap.

17. A stuffed, soft body scent-emitting toy, comprising:

a figurine defined by an exterior surface of a fabric material and having an internal cavity filled with a stuffing material to define a body thereof, a portion of the fabric material defining an opening therein;

a chamber having a bottom and side wall extending in a first direction therefrom and received in the opening of the figurine;

a pin extending radially from an inner wall surface near a distal edge of the side wall;

a cap hingedly connected at an edge portion to the side wall of the chamber for engaging the distal edge portion of the side wall of the chamber, the cap defining a plurality of spaced-apart openings for communicating air therethrough and a slot in an edge of the cap for alignment with the pin, whereby the cap, being pivoted closed on the hinge connection, is secured closed by engaging the pin in the slot of the cap, whereby the figurine, receiving a scent emittive material in the chamber closed by the cap, provides a soft toy that emits a scent through the openings.

18. The stuffed, soft body scent-emitting toy as recited in claim 17, further comprising means for changing the cross-sectional area of the openings in the plate, for changing the volume of scented air communicated through the openings.

* * * * *